(12) United States Patent
Liu et al.

(10) Patent No.: US 9,789,340 B2
(45) Date of Patent: Oct. 17, 2017

(54) FILTER AND NEUTRON BEAM SOURCE INCLUDING THE SAME

(71) Applicants: INDUSTRIAL TECHNOLOGY RESEARCH INSTITUTE, Hsinchu (TW); NATIONAL TSING HUA UNIVERSITY, Hsinchu (TW)

(72) Inventors: Yen-Wan Hsueh Liu, Hsinchu (TW); Zhen-Fan You, Sanxing Township (TW)

(73) Assignees: INDUSTRIAL TECHNOLOGY RESEARCH INSTITUTE, Hsinchu (TW); NATIONAL TSING HUA UNIVERSITY, Hsinchu (TW)

( * ) Notice: Subject to any disclaimer, the term of this patent is extended or adjusted under 35 U.S.C. 154(b) by 187 days.

(21) Appl. No.: 14/511,937

(22) Filed: Oct. 10, 2014

(65) Prior Publication Data
US 2015/0105604 A1 Apr. 16, 2015

(30) Foreign Application Priority Data

Oct. 15, 2013 (TW) .............................. 102137074 A

(51) Int. Cl.
*A61N 5/10* (2006.01)
*G21K 1/10* (2006.01)
*G21G 4/02* (2006.01)

(52) U.S. Cl.
CPC ............ *A61N 5/1077* (2013.01); *G21G 4/02* (2013.01); *A61N 2005/109* (2013.01); *A61N 2005/1095* (2013.01); *G21K 1/10* (2013.01)

(58) Field of Classification Search
None
See application file for complete search history.

(56) References Cited

U.S. PATENT DOCUMENTS

| | | | |
|---|---|---|---|
| 5,531,970 A | 7/1996 | Carlson | |
| 5,703,918 A * | 12/1997 | Hiismaki | A61N 5/10 376/458 |
| 5,903,622 A | 5/1999 | Yoon et al. | |

(Continued)

FOREIGN PATENT DOCUMENTS

| | | |
|---|---|---|
| CN | 101529530 A | 9/2009 |
| CN | 102855954 A | 1/2013 |

(Continued)

OTHER PUBLICATIONS

Rahmani et al., "Beam shaping assembly optimization of Linac based BNCT and in-phantom depth dose distribution analysis of brain tumors for verification of a beam model", Annals of Nuclear Energy, vol. 38, 2-3, Feb.-Mar. 2011.*

(Continued)

*Primary Examiner* — Jason McCormack
*Assistant Examiner* — James Choi
(74) *Attorney, Agent, or Firm* — Birch, Stewart, Kolasch & Birch, LLP

(57) ABSTRACT

Disclosed is a filter including a second layer disposed between a first layer and a third layer. The first layer is composed of iron. The second layer is composed of 1 part by volume of lithium fluoride, 20 to 50 parts by volume of aluminum, and 50 to 80 parts by volume of aluminum fluoride. The third layer is composed of 1 part by weight of lithium fluoride and 99 to 100 parts by weight of magnesium fluoride.

16 Claims, 3 Drawing Sheets

(56) References Cited

U.S. PATENT DOCUMENTS

| | | |
|---|---|---|
| 8,148,922 B2 | 4/2012 | Cleland et al. |
| 8,217,360 B2 | 7/2012 | Nukatsuka et al. |
| 2010/0025594 A1 | 2/2010 | Nukasuka et al. |
| 2010/0200758 A1 | 8/2010 | Fukuda et al. |
| 2012/0018642 A1 | 1/2012 | Fukuda et al. |
| 2013/0129027 A1 | 5/2013 | Pantell et al. |

FOREIGN PATENT DOCUMENTS

| | | | |
|---|---|---|---|
| CN | WO 2016177270 A1 * | 11/2016 | ............... A61N 5/00 |
| EP | 1895819 A1 | 3/2008 | |
| JP | 02054192 A * | 2/1990 | |
| JP | 2013-208257 A | 10/2013 | |

OTHER PUBLICATIONS

Shigehiro et al., "Development Studies Regarding the Construction of Epithermal Enriched Neutron Field for Medical Purposes at the University of Tokyo Yayoi Fast Reactor", Nuclear Technology, vol. 48, May 1980.*

Kasesaz et al., "Optimization of the beam shaping assembly in the D-D neutron generators-based BNCT using the response matrix method", Applied Radiation and Isotopes, 82, 2013.*

Tanaka et al., "Characteristics comparison between a cyclotron-based neutron source and KUR-HWNIF for boron neutron capture therapy", Nuclear Instruments and Methods in Physics Research B 267, 2009.*

Burlon et al., "Design of a beam shaping assembly and preliminary modelling of a treatment room for accelerator-based BNCT at CNEA", Elsevier, Applied Radiation and Isotopes 69, pp. 1688-1691, (2011).

Ceballos, et al., "Towards the final BSA modeling for the accelerator-driven BNCT facility at INFN LNL", Elsevier, Applied Radiation and Isotopes, 69 pp. 1660-1663, (2011).

Forton et al., 13. E. Forton et al., "Overview of the IBA accelerator-based BNCT system", Elsevier, Applied Radiation and Isotopes 67, pp. S262-S265, (2009).

Inoue et al., "Optimum design of a moderator system based on dose calculation for an accelerator driven Boron Neutron Capture Therapy", Elsevier, Applied Radiation and Isotopes vol. 88, pp. 225-228, (2014).

Kandiev et al., "Optimization of the Target of an Accelerator-Driven Neutron Source through Monte Carlo Numerical Simulation of Neutron and Gamma Transport by the PRIZMA Code," Elsevier, Applied Radiation and Isotopes 69, pp. 1632-1634, (2011).

Rahmani et al., "Beam shaping assembly optimization of Linac based BNCT and in-phantom depth dose distribution analysis of brain tumors for verification of a beam model", Elsevier, Annals of Nuclear Energy 38, pp. 404-409, (2011).

Takata et al., "Increase in Irradiation Beam Intensity by Using a Hybrid Target System in Cyclotron-Based Neutron Capture Therapy" Journal of Nuclear Science and Technology, vol. 47, Issue 7, pp. 575-581, (2010).

Tanaka et al. "A TPD and AD based comparison of accelerator neutron irradiation field between 7Li and W tragets for BNCT", Elsevier, Applied Radiation and Isotopes 88, pp. 229-232, (2014).

Salehi et al., "Evaluation of Design Neutron Filters in BNCT," Open Access Scientific Reports, vol. 1, Issue 11, Sep. 28, 2012, pp. 1-6.

Taiwanese Office Action and Search Report for Taiwanese Application No. 102137074, dated Dec. 15, 2015.

* cited by examiner

FILTER AND NEUTRON BEAM SOURCE INCLUDING THE SAME

CROSS REFERENCE TO RELATED APPLICATIONS

The present application is based on, and claims priority from, Taiwan Application Serial Number 102137074, filed on Oct. 15, 2013, the disclosure of which is hereby incorporated by reference herein in its entirety

TECHNICAL FIELD

The technical field relates to a neutron beam source, and in particular to a filter for producing a neutron beam.

BACKGROUND

In the principle of the boron neutron capture therapy (BNCT), a boron-containing drug is preferentially accumulated in tumor cells through the blood circulation, and the tumor tissue is irradiated by a neutron beam. As such, the boron absorbs neutron to produce high LET alpha particle and $^7Li$ ion, which may locally destroy the tumor cells without damaging the normal tissues.

BNCT only causes extremely small damage to the patient, and the surgical operation and anesthetic can be omitted. If thermal neutrons are used in BNCT for a brain tumor, the skull of the patient needs to be opened up. If epithermal neutrons are used in BNCT for the brain tumor, the step of opening the skull can be omitted.

Most of the neutron beam sources in BNCT are from research reactors. In general, research reactors cannot be located in hospitals, and therefore the doctors and patients must move to the location of research reactors. On the other hand, accelerator-based neutron beam sources can be built in hospitals. It not only costs less, but also saves time for the doctors and the patients.

Accordingly, an accelerator-based neutron beam source for BNCT is called for.

SUMMARY

One embodiment of the disclosure provides a filter, comprising: a first layer composed of iron; a second layer composed of 1 part by volume of lithium fluoride, 20 to 50 parts by volume of aluminum, and 50 to 80 parts by volume of aluminum fluoride; and a third layer composed of 1 part by weight of lithium fluoride and 99 to 100 parts by weight of magnesium fluoride, wherein the second layer is disposed between the first layer and the third layer.

One embodiment of the disclosure provides a neutron beam source, comprising: an accelerator; a beryllium target; and the described filter, wherein the beryllium target is disposed between the accelerator and the filter, and the first layer of the filter is disposed between the beryllium target and the third layer.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
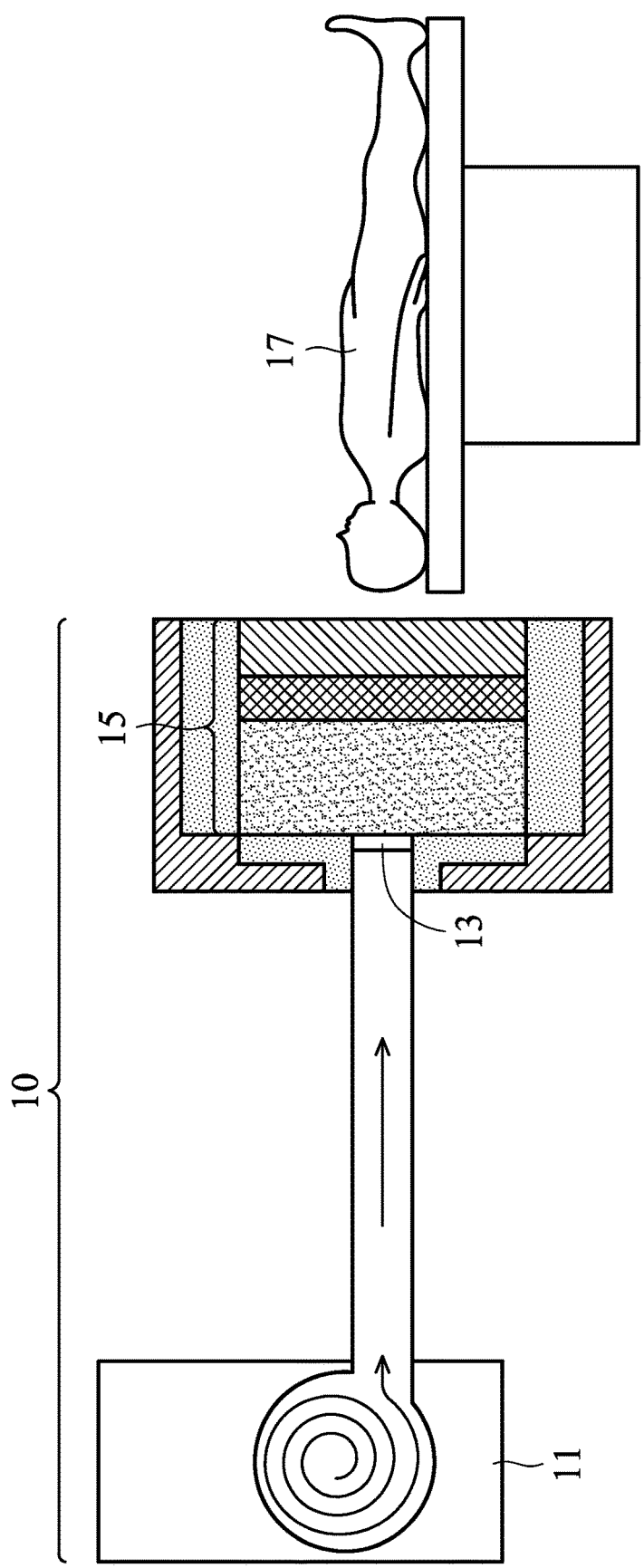
FIG. 1 shows a neutron beam source in one embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

As shown in FIG. 1, a neutron beam source 10 in one embodiment of the disclosure is constructed from three principal parts: an accelerator 11, a target 13, and a filter 15, wherein the target 13 is disposed between the accelerator 11 and the filter 15. For example, the accelerator 11 can be a cyclotron commercially available from Sumitomo Heavy Industries. The accelerator 11 is used to provide protons with energy of about 30 MeV and a current of greater than or equal to 1 mA to collide with the target 13, thereby producing fast neutrons. The fast neutrons pass through the filter 15 turning into an epithermal neutron beam. The International Atomic Energy Agency (IAEA) suggests that a desirable minimum epithermal neutron beam intensity for BNCT would be $10^9$ epithermal neutrons $cm^{-2} \cdot s^{-1}$, and the fast neutron dose component and the gamma ray dose component would be less than $2.0 \times 10^{-11}$ cGy $cm^2$ per epithermal neutron. Since the criterion for gamma ray dose component is easily achieved, the disclosure mainly discusses the epithermal neutron flux and the fast neutron dose component. An overly low epithermal neutron flux may prolong the irradiation time of the therapy for a patient 17. An overly high fast neutron flux may damage the normal tissues of the patient 17. The protons (produced by the accelerator 11) with overly high energy will increase the difficulty of shielding design without further increasing the neutron yield. The protons (produced by the accelerator 11) with overly low energy may produce neutrons of insufficient yield, and the current of the protons would need to be increased to compensate for the neutron yield.

In one embodiment, the target 13 is composed of beryllium with a thickness of 0.55 cm to 0.58 cm. An overly thick target 13 cannot easily dissipate heat. An overly thin target 13 decreases the neutron yield.

In one embodiment of the disclosure, the filter 15 has a total thickness of 67.5 cm to 70 cm, and a cross-section area of 0.5 $m^2$ to 1.13 $m^2$ (e.g. a circle with a radius of 40 cm to 60 cm). A filter 15 with an overly thin total thickness cannot efficiently reduce the fast neutron dose component. A filter 15 with an overly thick total thickness cannot produce sufficient epithermal neutron flux. A filter with an overly large cross-section area will increase the filter weight and cost, and reduce the average epithermal neutron flux without improving the neutron beam quality. A filter 15 (having the same thickness as a filter with a proper cross-section area) with an overly small cross-section area cannot efficiently reduce the fast neutron dose component.

Figure 2:
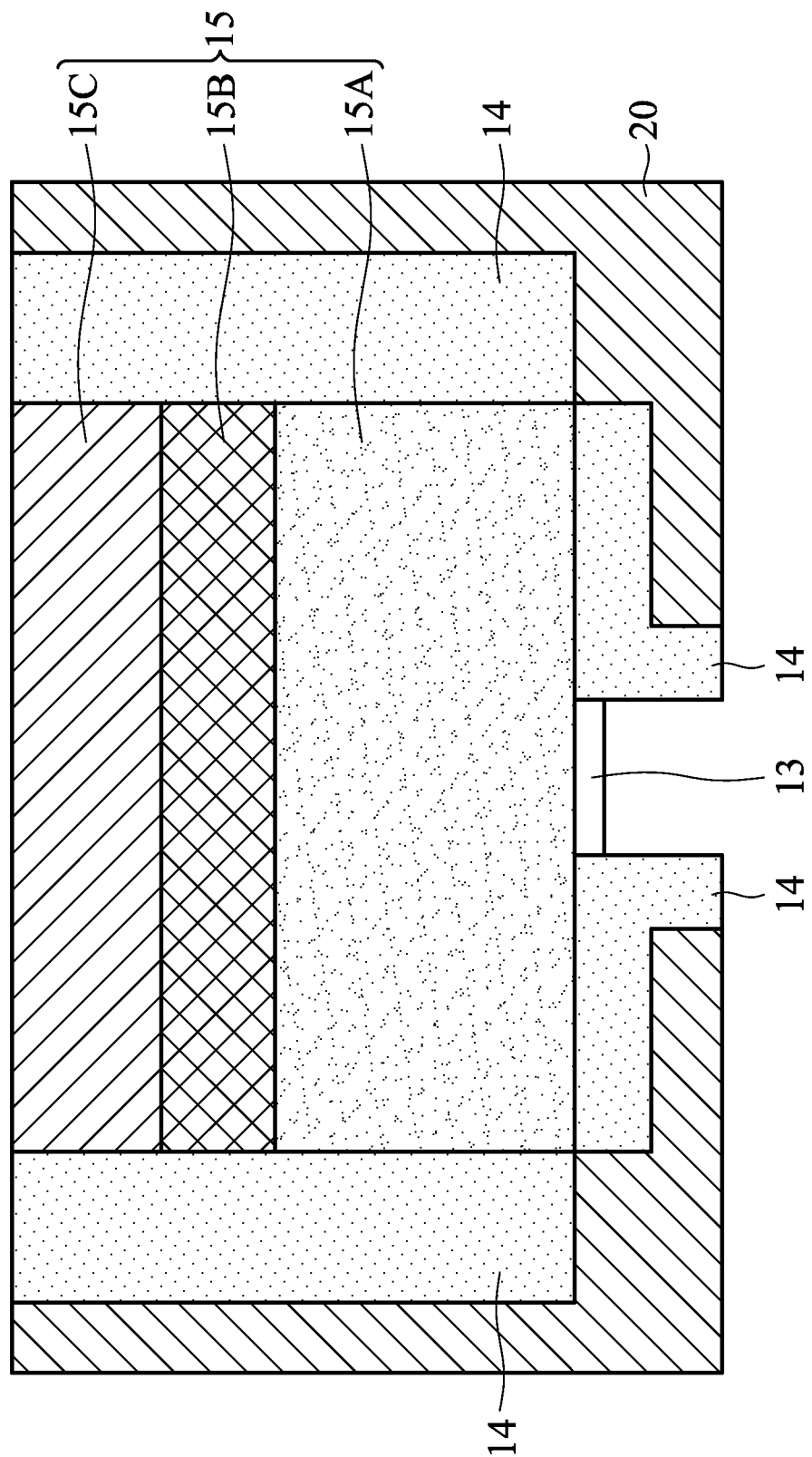
FIG. 2 shows a filter in one embodiment of the disclosure.

As shown in FIG. 2, the filter 15 is a tri-layered structure. The second layer 15B is disposed between a first layer 15A and a third layer 15C, and the first layer 15A is disposed between the target 13 and the third layer 15C. As the protons collide with the target 13 neutrons are produced, which sequentially pass through the first layer 15A, the second layer 15B, and the third layer 15C. The first layer 15A is composed of iron. The neutrons with energy higher than 1 MeV will be moderated to energy less than 1 MeV by inelastic scattering with iron. In one embodiment of the disclosure, the first layer 15A has a thickness of 25 cm to 40 cm. A first layer 15A with an overly thin thickness will cause too many neutrons having energy higher than 1 MeV. A first layer 15A with an overly thick thickness will reduce thicknesses of other layers for shaping the neutrons with energy less than 1 MeV, thereby affecting the neutron beam quality.

The second layer 15B is composed of 1 part by volume of lithium fluoride, 20 to 50 parts by volume of aluminum, and 50 to 80 parts by volume of aluminum fluoride. For example, the second layer 15B can be referred to U.S. Pat. No. 5,703,918. In one embodiment, the second layer 15B has a thickness of 10 cm to 37.5 cm. When the total thickness of the filter 15 is fixed, a second layer 15B with an overly thick thickness will result in an overly thin third layer, thereby fail to sufficiently moderate the neutrons and results in an overly high fast neutron dose rate. A second layer 15B with an overly thin thickness will cause an overly thick third layer. The fast neutron dose rate of the neutron beam can be sufficiently reduced. However, the epithermal neutron flux will be overly low. The third layer 15C is composed of 1 part by weight of lithium fluoride and 99 to 100 parts by weight of magnesium fluoride. An overly low percentage of the lithium fluoride and an overly high percentage of the magnesium fluoride will produce a neutron beam with an overly high thermal neutron flux. An overly high percentage of the lithium fluoride and an overly low percentage of the magnesium fluoride will produce a neutron beam with an overly high fast neutron dose per epithermal neutron. In one embodiment, the third layer 15C has a thickness of 5 cm to 20 cm. A third layer 15C with an overly thick thickness will overly moderate the neutrons, thereby producing a neutron beam with an overly low epithermal neutron flux. A third layer 15C with an overly thin thickness will be insufficient to moderate the neutrons, thereby producing a neutron beam with an overly high fast neutron dose rate.

In one embodiment, a lead wall 14 with a thickness of greater than 15 cm can be disposed outside the filter 15 to further increase the final epithermal neutron flux. An overly thick lead wall 14 will be over weighted. The filter 15 can be surrounded by a shield 20 to avoid radiation penetrating out of the filter 15. In one embodiment, the shield 20 can be concrete.

In one embodiment, the accelerator 11 produces a proton beam of 30 MeV/1 mA, and the neutron beam source 10 correspondingly produces a neutron beam having an epithermal neutron flux of $1.7 \times 10^9$ n cm$^{-2}$s$^{-1}$ to $1.9 \times 10^9$ n cm$^{-2}$s$^{-1}$, and a fast neutron dose component of $2.9 \times 10^{-11}$ cGy cm$^2$ to $3.5 \times 10^{-11}$ cGy cm$^2$ per epithermal neutron.

Figure 3:
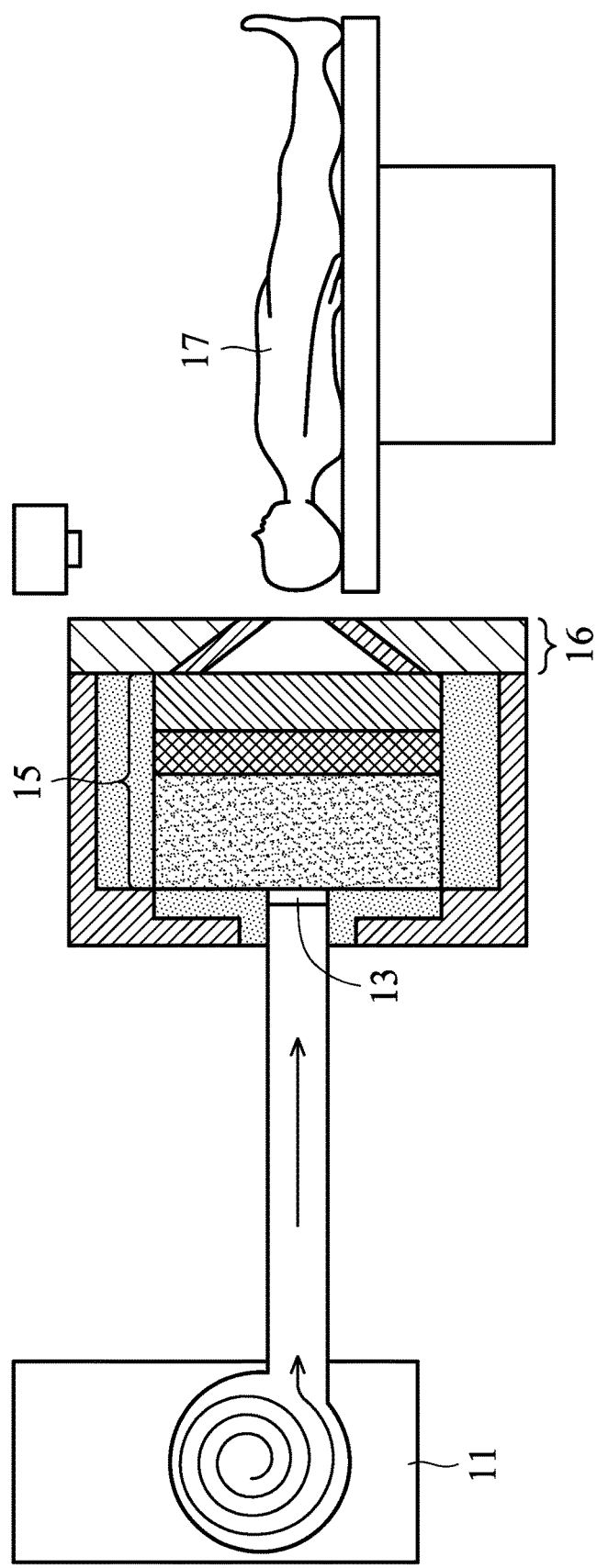
FIG. 3 shows a neutron beam source containing a collimator element in one embodiment of the disclosure.

In one embodiment, a collimator element 16 can be added as shown in FIG. 3. The collimator element is located between the patient 17 and the filter 15, and the filter 15 is located between the collimator element 16 and the target 13. The design of the collimator element 16 can be referred in Y-W H. Liu, T. T. Huang, S. H. Jiang, H. M. Liu, (2004) "Renovation of Epithermal Neutron Beam for BNCT at THOR," Appl. Radiat. Isot. 61, 1039-1043. The collimator element 16 may focus and maintain the epithermal neutron flux intensity, and simultaneously reduce the fast neutron dose rate. For example, the accelerator 11 produces a proton beam of 30 MeV/1 mA, and the neutron beam source 10 with the collimator element 16 correspondingly produces a neutron beam having an epithermal neutron flux of $1.7 \times 10^9$ n cm$^{-2}$s$^{-1}$ to $2.0 \times 10^9$ n cm$^{-2}$s$^{-1}$, and a fast neutron dose component of $2.0 \times 10^{-11}$ cGy cm$^2$ to $2.6 \times 10^{-11}$ cGy cm$^2$ per epithermal neutron. When the accelerator 11 produces a proton beam of 30 MeV/2 mA, the neutron beam source 10 with the collimator element 16 correspondingly produces a neutron beam having a double epithermal neutron flux (e.g. $3.4 \times 10^9$ n cm$^{-2}$s$^{-1}$ to $4.0 \times 10^9$ n cm$^{-2}$s$^{-1}$), a double fast neutron dose rate, compared to that from a proton beam of 30 MeV/1 mA. The fast neutron dose component remains the same ($2.0 \times 10^{-11}$ cGy cm$^2$ to $2.6 \times 10^{-11}$ cGy cm$^2$ per epithermal neutron). Because the neutron beam source 10 can produce sufficient epithermal neutron flux and a low fast neutron dose rate, the neutron beam source 10 is suitable for use in accelerator-based BNCT.

If the proton energy produced by the accelerator changes, the thickness ranges of the three layers in the filter for producing ideal epithermal neutrons will change slightly.

When the energy of the protons produced by the accelerator increases to 31 MeV/1 mA, the filter for producing ideal epithermal neutrons has a tri-layered structure as follows: a first layer with a thickness of 27.5 cm to 40 cm, a second layer with a thickness of 10 cm to 35 cm, and a third layer with a thickness of 7.5 cm to 20 cm. In one embodiment, the neutron beam source 10 produces a neutron beam having an epithermal neutron flux of $1.7 \times 10^9$ n cm$^{-2}$s$^{-1}$ to $1.9 \times 10^9$ n cm$^{-2}$s$^{-1}$, and a fast neutron dose component of $2.9 \times 10^{-11}$ cGy cm$^2$ to $3.7 \times 10^{-11}$ cGy cm$^2$ per epithermal neutron.

When the energy of protons produced by the accelerator decreases to 29 MeV/1 mA, the filter for producing ideal epithermal neutrons has a tri-layered structure as below: a first layer with a thickness of 25 cm to 37.5 cm, a second layer with a thickness of 12.5 cm to 37.5 cm, and a third layer with a thickness of 5 cm to 17.5 cm. In one embodiment, the neutron beam source 10 produces a neutron beam having an epithermal neutron flux of $1.7 \times 10^9$ n cm$^{-2}$s$^{-1}$ to $1.9 \times 10^9$ n cm$^{-2}$s$^{-1}$, and a fast neutron dose component of $2.9 \times 10^{-11}$ cGy cm$^2$ to $3.5 \times 10^{-11}$ cGy cm$^2$ per epithermal neutron.

Below, exemplary embodiments will be described in detail with reference to accompanying drawings for easy understanding. The inventive concept may be embodied in various forms without being limited to the exemplary embodiments set forth herein. Descriptions of well-known parts are omitted for clarity, and like reference numerals refer to like elements throughout.

EXAMPLES

In the experiments described below, the simulation calculation software used MCNPX, developed by Los Alamos National Laboratory, and the cross-section library was ENDF/B-7.

In Examples 1 to 4, the accelerator produced protons of 30 MeV/1 mA, and the target was beryllium with a thickness of 0.55 cm. The first layer of the filter was composed of iron. The second layer of the filter was composed of 1 part by weight of lithium fluoride, 30 parts by weight of aluminum, and 69 parts by weight of aluminum fluoride (equal to 1 part by volume of lithium fluoride, 31 parts by volume of aluminum, and 68 parts by volume of aluminum fluoride). The third layer of the filter was composed of 1 part by weight of lithium fluoride and 99 parts by weight of magnesium fluoride.

Example 1

The first layer, the second layer, and the third layer, each with a different thickness, were selected to construct filters having a circular cross-section with a radius of 50 cm. The epithermal neutron flux, the fast neutron dose rate, and the fast neutron dose per epithermal neutron of the neutron beams produced by neutron beam sources containing the filters are tabulated in Table 1.

TABLE 1

| | Example 1-1 | Example 1-2 | Example 1-3 | Example 1-4 | Example 1-5 |
|---|---|---|---|---|---|
| Filter structure | First layer (30 cm) + second layer (35 cm) | First layer (30 cm) + second layer (40 cm) | First layer (30 cm) + second layer (42.5 cm) | First layer (30 cm) + Third layer (35 cm) | First layer (30 cm) + second layer (25 cm) + third layer (12.5 cm) |
| Epithermal neutron flux (n cm$^{-2}$ · s$^{-1}$) (1 standard deviation) | 2.33 × 10$^9$ (0.08%) | 2.02 × 10$^9$ (0.09%) | 1.86 × 10$^9$ (0.09%) | 1.55 × 10$^9$ (0.10%) | 1.89 × 10$^9$ (0.09%) |
| Fast neutron dose rate (cGy · s$^{-1}$) (1 standard deviation) | 0.146 (0.4%) | 0.083 (0.51%) | 0.063 (0.61%) | 0.052 (0.83%) | 0.065 (0.67%) |
| Fast neutron dose per epithermal neutron (cGy · cm$^2$/n) | 6.27 × 10$^{-11}$ | 4.13 × 10$^{-11}$ | 3.40 × 10$^{-11}$ | 3.39 × 10$^{-11}$ | 3.46 × 10$^{-11}$ |

As shown in Table 1, the atomic mass of the aluminum in the second layer was large, therefore, it could not effectively slow down the fast neutrons. As such, the second layer should be thickened to reduce the fast neutron dose rate. But the thicker second layer also reduced the epithermal neutron flux. The atomic mass of the magnesium in the third layer was smaller, therefore, it could slow down the fast neutrons effectively. However, it also reduced the epithermal neutron flux. When the total thickness of the first layer and the second layer (e.g. Example 1-1) was the same as the total thickness of the first layer and the third layer (e.g. Example 1-4), the epithermal neutron flux in Example 1-4 was less than the epithermal neutron flux in Example 1-1. As shown in the comparison between Examples 1-3 and 1-4, the second layer in the filter composed of the first layer and the second layer should be 7.5 cm thicker than the third layer in the filter composed of the first layer and the third layer in order to achieve approximately the same fast neutron dose rate. By comparing Examples 1-3, 1-4, and 1-5, it is shown that for achieving an approximately the same and reasonably low value of fast neutron dose per epithermal neutron, the tri-layered filter in Example 1-5 not only produced a higher epithermal neutron flux, but also had a total thickness being 5 cm thinner than the bi-layered filter in Example 1-3.

Example 2

Example 2-1 was similar to Example 1-5, and the difference in Example 2-1 was that the positions of the second layer and the third layer were exchanged. Although the epithermal neutron flux in Example 2-1 was higher than that in Example 1-5, the fast neutron dose in Example 2-1 was also higher than that in Example 1-5. For reducing the fast neutron dose rate in Example 2-1, the thickness of the third layer was increased in Example 2-2. Although the fast neutron dose rate in Example 2-2 is similar to that in Example 1-5, the epithermal neutron flux in Example 2-2 is also reduced. Accordingly, the position arrangement of the first layer, the second layer, and the third layer in Example 1-5 is better than the position arrangement of the first layer, the third layer, and the second layer in Examples 2-1 and 2-2.

TABLE 2

| | Example 1-5 | Example 2-1 | Example 2-2 |
|---|---|---|---|
| Filter structure | First layer (30 cm) + second layer (25 cm) + third layer (12.5 cm) | First layer (30 cm) + third layer (12.5 cm) + second layer (25 cm) | First layer (30 cm) + third layer (14 cm) + second layer (25 cm) |
| Epithermal neutron flux (n cm$^{-2}$ · s$^{-1}$) (1 standard deviation) | 1.89 × 10$^9$ (0.09%) | 1.96 × 10$^9$ (0.09%) | 1.82 × 10$^9$ (0.09%) |
| Fast neutron dose rate (cGy · s$^{-1}$) (1 standard deviation) | 0.065 (0.67%) | 0.077 (0.59%) | 0.063 (0.62%) |
| Fast neutron dose per epithermal neutron (cGy · cm$^2$/n) | 3.46 × 10$^{-11}$ | 3.91 × 10$^{-11}$ | 3.44 × 10$^{-11}$ |

Example 3

The first layer of fixed thickness (30 cm) was followed by different thickness of second layer and third layer to construct a circular filter with a radius of 50 cm. The filter was further added with a collimator element disclosed in Y-W H. Liu, T. T. Huang, S. H. Jiang, H. M. Liu, (2004) "Renovation of Epithermal Neutron Beam for BNCT at THOR," Appl. Radiat. Isot. 61, 1039-1043. The epithermal neutron flux, the fast neutron dose rate, and the fast neutron dose per epithermal neutron of the neutron beams produced by neutron beam sources containing the filters and the collimator element are tabulated in Table 3.

TABLE 3

| | Example 3-1 | Example 3-2 | Example 3-3 | Example 3-4 |
|---|---|---|---|---|
| Filter structure | First layer (30 cm) + second layer (42.5 cm) | First layer (30 cm) + third layer (35 cm) | First layer (30 cm) + third layer (14 cm) + second layer (25 cm) | First layer (30 cm) + second layer (25 cm) + third layer (12.5 cm) |
| Epithermal neutron flux (n cm$^{-2}$ · s$^{-1}$) (1 standard deviation) | 1.92 × 10$^9$ (0.18%) | 1.58 × 10$^9$ (0.20%) | 1.86 × 10$^9$ (0.19%) | 1.99 × 10$^9$ (0.18%) |

TABLE 3-continued

|  | Example 3-1 | Example 3-2 | Example 3-3 | Example 3-4 |
|---|---|---|---|---|
| Fast neutron dose rate (cGy · s$^{-1}$) (1 standard deviation) | 0.043 (1.41%) | 0.043 (1.80%) | 0.046 (1.46%) | 0.050 (1.50%) |
| Fast neutron dose per epithermal neutron) (cGy · cm$^2$/n) | 2.25 × 10$^{-11}$ | 2.70 × 10$^{-11}$ | 2.45 × 10$^{-11}$ | 2.51 × 10$^{-11}$ |

By comparing the results in Table 3 with Table 1 and Table 2, it is seen that the collimator element can maintain the epithermal neutron flux intensity and reduce the fast neutron dose rate to a value close to that suggested by IAEA.

Example 4

Different thicknesses of the first layer, the second layer, and the third layer were selected to construct filters having a circular cross-section with a radius of 50 cm. No collimator element was adopted in this Example. The epithermal neutron flux, the fast neutron dose rate, and the fast neutron dose per epithermal neutron of the neutron beams produced by neutron beam sources containing the filters are tabulated in Table 4.

TABLE 4

| Proton 30 MeV/1 mA | Filter structure | | | Epithermal neutron flux (n cm$^{-2}$ · s$^{-1}$) (1 standard deviation) | Fast neutron dose rate (cGy · s$^{-1}$) (1 standard deviation) | Fast neutron dose per epithermal neutron (cGy · cm$^2$/n) |
|---|---|---|---|---|---|---|
|  | First layer (cm) | Second layer (cm) | Third layer (cm) |  |  |  |
| Example 4-1 | 30 | 35 | 5 | 1.89 × 10$^9$ (0.09%) | 0.064 (0.63%) | 3.41 × 10$^{-11}$ |
| Example 4-2 | 30 | 25 | 12.5 | 1.89 × 10$^9$ (0.09%) | 0.065 (0.67%) | 3.46 × 10$^{-11}$ |
| Example 4-3 | 25 | 37.5 | 7.5 | 1.84 × 10$^9$ (0.07%) | 0.058 (0.52%) | 3.15 × 10$^{-11}$ |
| Example 4-4 | 35 | 25 | 10 | 1.80 × 10$^9$ (0.09%) | 0.060 (0.61%) | 3.30 × 10$^{-11}$ |
| Example 4-5 | 35 | 15 | 17.5 | 1.80 × 10$^{99}$ (0.09%) | 0.062 (0.61%) | 3.43 × 10$^{-11}$ |
| Example 4-6 | 37.5 | 10 | 20 | 1.79 × 10$^9$ (0.07%) | 0.062 (0.41%) | 3.44 × 10$^{-11}$ |
| Example 4-7 | 30 | 30 | 10 | 1.78 × 10$^9$ (0.09%) | 0.054 (0.74%) | 3.03 × 10$^{-11}$ |
| Example 4-8 | 30 | 20 | 17.5 | 1.76 × 10$^9$ (0.10%) | 0.056 (0.73%) | 3.17 × 10$^{-11}$ |
| Example 4-9 | 40 | 15 | 15 | 1.75 × 10$^9$ (0.07%) | 0.060 (0.39%) | 3.43 × 10$^{-11}$ |
| Example 4-10 | 35 | 12.5 | 20 | 1.74 × 10$^9$ (0.10%) | 0.057 (0.68%) | 3.29 × 10$^{-11}$ |
| Example 4-11 | 30 | 27.5 | 12.5 | 1.72 × 10$^9$ (0.10%) | 0.050 (0.77%) | 2.90 × 10$^{-11}$ |
| Example 4-12 | 35 | 20 | 15 | 1.70 × 10$^9$ (0.10%) | 0.050 (0.69%) | 2.94 × 10$^{-11}$ |
| Example 4-13 | 30 | 17.5 | 20 | 1.70 × 10$^9$ (0.10%) | 0.054 (0.80%) | 3.17 × 10$^{-11}$ |

As shown in Table 4, the neutron beam source with the filter (having the first layer, the second layer, and the third layer with proper thicknesses) provided sufficient epithermal neutron flux and low fast neutron dose rate.

Example 5

For accelerator producing protons of 31 MeV/1 mA, different thicknesses of the first layer, the second layer, and the third layer were selected to construct filters having a circular cross-section with a radius of 50 cm. No collimator element was adopted in this Example. The epithermal neutron flux, the fast neutron dose rate, and the fast neutron dose per epithermal neutron of the neutron beams produced by neutron beam sources containing the filters are tabulated in Table 5.

TABLE 5

| Proton 31 MeV/1 mA | Filter structure | | | Epithermal neutron flux ($n\ cm^{-2} \cdot s^{-1}$) (1 standard deviation) | Fast neutron dose rate ($cGy \cdot s^{-1}$) (1 standard deviation) | Fast neutron dose per epithermal neutron ($cGy \cdot cm^2/n$) |
|---|---|---|---|---|---|---|
| | First layer (cm) | Second layer (cm) | Third layer (cm) | | | |
| Example 5-1 | 27.5 | 35 | 7.5 | $1.86 \times 10^9$ (0.12%) | 0.062 (0.90%) | $3.35 \times 10^{-11}$ |
| Example 5-2 | 37.5 | 10 | 20 | $1.79 \times 10^9$ (0.12%) | 0.065 (0.77%) | $3.64 \times 10^{-11}$ |
| Example 5-3 | 40 | 15 | 15 | $1.74 \times 10^9$ (0.12%) | 0.062 (0.72%) | $3.56 \times 10^{-11}$ |

Example 6

For accelerator producing protons of 29 MeV, 1 mA, different thicknesses of the first layer, the second layer, and the third layer were selected to construct filters having a circular cross-section with a radius of 50 cm. No collimator element was adopted in this Example. The epithermal neutron flux, the fast neutron dose rate, and the fast neutron dose per epithermal neutron of the neutron beams produced by neutron beam sources containing the filters are tabulated in Table 6.

TABLE 6

| Proton 29 MeV/1 mA | Filter structure | | | Epithermal neutron flux ($n\ cm^{-2} \cdot s^{-1}$) (1 standard deviation) | Fast neutron dose rate ($cGy \cdot s^{-1}$) (1 standard deviation) | Fast neutron dose per epithermal neutron ($cGy \cdot cm^2/n$) |
|---|---|---|---|---|---|---|
| | First layer (cm) | Second layer (cm) | Third layer (cm) | | | |
| Example 6-1 | 25 | 37.5 | 7.5 | $1.71 \times 10^9$ (0.12%) | 0.050 (1.04%) | $2.91 \times 10^{-11}$ |
| Example 6-2 | 30 | 35 | 5 | $1.81 \times 10^9$ (0.12%) | 0.056 (0.88%) | $3.09 \times 10^{-11}$ |
| Example 6-3 | 37.5 | 12.5 | 17.5 | $1.72 \times 10^9$ (0.12%) | 0.060 (0.73%) | $3.47 \times 10^{-11}$ |

Example 7

For accelerator producing protons of 30 MeV/1 mA, different thicknesses of the first layer, the second layer, and the third layer were selected to construct filters having a circular cross-section with a radius of 50 cm. The collimator element in Example 3 was adopted in this Example. The epithermal neutron flux, the fast neutron dose rate, and the fast neutron dose per epithermal neutron of the neutron beams produced by neutron beam sources containing the filters after passing through the collimator are tabulated in Table 7.

TABLE 7

| Proton 30 MeV/1 mA | Filter structure | | | Epithermal neutron flux (n cm$^{-2}$ · s$^{-1}$) (1 standard deviation) | Fast neutron dose rate (cGy · s$^{-1}$) (1 standard deviation) | Fast neutron dose per epithermal neutron (cGy · cm$^2$/n) |
|---|---|---|---|---|---|---|
| | First layer (cm) | Second layer (cm) | Third layer (cm) | | | |
| Example 7-1 | 25 | 37.5 | 7.5 | 1.79 × 10$^9$ (0.08%) | 0.046 (0.77%) | 2.55 × 10$^{-11}$ |
| Example 7-2 | 30 | 35 | 5 | 2.01 × 10$^9$ (0.07%) | 0.047 (0.69%) | 2.34 × 10$^{-11}$ |
| Example 7-3 | 40 | 15 | 15 | 1.87 × 10$^9$ (0.07%) | 0.038 (0.65%) | 2.03 × 10$^{-11}$ |
| Example 7-4 | 37.5 | 10 | 20 | 1.90 × 10$^9$ (0.07%) | 0.042 (0.69%) | 2.21 × 10$^{-11}$ |

It will be apparent to those skilled in the art that various modifications and variations can be made to the disclosed methods and materials. It is intended that the specification and examples be considered as exemplary only, with a true scope of the disclosure being indicated by the following claims and their equivalents.

What is claimed is:

1. A neutron beam filter, comprising:
   a first layer composed of iron;
   a second layer composed of 1 part by volume of lithium fluoride, 20 to 50 parts by volume of aluminum, and 50 to 80 parts by volume of aluminum fluoride; and
   a third layer composed of 1 part by weight of lithium fluoride and 99 to 100 parts by weight of magnesium fluoride, wherein the lithium fluoride is dispersed in the magnesium fluoride,
   wherein the second layer is disposed between the first layer and the third layer, and
   wherein the neutron beam filter is configured to form a moderated neutron beam.

2. The neutron beam filter as claimed in claim 1, wherein the filter has a total thickness of 67.5 cm to 70 cm, and a circular cross-section with a radius of 40 cm to 60 cm.

3. The neutron beam filter as claimed in claim 1, wherein the first layer has a thickness of 25 cm to 40 cm, the second layer has a thickness of 10 cm to 37.5 cm, and the third layer has a thickness of 5 cm to 20 cm.

4. A neutron beam source, comprising:
   an accelerator;
   a beryllium target; and
   the filter as claimed in claim 1,
   wherein the beryllium target is disposed between the accelerator and the filter, and the first layer of the filter is disposed between the beryllium target and the third layer.

5. The neutron beam source as claimed in claim 4, wherein:
   the accelerator produces a proton beam of 30 MeV/1 mA, the first layer of the filter has a thickness of 25 cm to 40 cm, the second layer of the filter has a thickness of 10 cm to 37.5 cm, and the third layer of the filter has a thickness of 5 cm to 20 cm.

6. The neutron beam source as claimed in claim 4, wherein:
   the accelerator produces a proton beam of 29 MeV/1 mA, the first layer of the filter has a thickness of 25 cm to 37.5 cm, the second layer of the filter has a thickness of 12.5 cm to 37.5 cm, and the third layer of the filter has a thickness of 5 cm to 17.5 cm.

7. The neutron beam source as claimed in claim 4, wherein:
   the accelerator produces a proton beam of 31 MeV/1 mA, the first layer of the filter has a thickness of 27.5 cm to 40 cm, the second layer of the filter has a thickness of 10 cm to 35 cm, and the third layer of the filter has a thickness of 7.5 cm to 20 cm.

8. The neutron beam source as claimed in claim 4, wherein:
   the accelerator produces a proton beam of 30 MeV/1 mA for colliding the beryllium target to form neutrons; and
   the neutrons pass through the filter to form a moderated neutron beam, wherein the moderated neutron beam has an epithermal neutron flux of $1.7 \times 10^9$ n cm$^{-2}$s$^{-1}$ to $1.9 \times 10^9$ n cm$^{-2}$s$^{-1}$, and a fast neutron dose component of $2.9 \times 10^{-11}$ cGy cm$^2$ to $3.5 \times 10^{-11}$ cGy cm$^2$ per epithermal neutron.

9. The neutron beam source as claimed in claim 4, wherein:
   the accelerator produces a proton beam of 29 MeV/1 mA for colliding the beryllium target to form neutrons; and
   the neutrons pass through the filter to form a moderated neutron beam, wherein the moderated neutron beam has an epithermal neutron flux of $1.7 \times 10^9$ n cm$^{-2}$s$^{-1}$ to $1.9 \times 10^9$ n cm$^{-2}$s$^{-1}$, and a fast neutron dose component of $2.9 \times 10^{-11}$ cGy cm$^2$ to $3.5 \times 10^{-11}$ cGy cm$^2$ per epithermal neutron.

10. The neutron beam source as claimed in claim 4, wherein:
    the accelerator produces a proton beam of 31 MeV/1 mA for colliding the beryllium target to form neutrons; and
    the neutrons pass through the filter to form a moderated neutron beam, wherein the moderated neutron beam has an epithermal neutron flux of $1.7 \times 10^9$ n cm$^{-2}$s$^{-1}$ to $1.9 \times 10^9$ n cm$^{-2}$s$^{-1}$, and a fast neutron dose component of $2.9 \times 10^{-11}$ cGy cm$^2$ to $3.7 \times 10^{-11}$ cGy cm$^2$ per epithermal neutron.

11. The neutron beam source as claimed in claim 4, further comprising a collimator element, wherein the filter is disposed between the beryllium target and the collimator element.

12. The neutron beam source as claimed in claim 11, wherein:

the accelerator produces a proton beam of 30 MeV/1 mA for colliding the beryllium target to form neutrons; and the neutrons pass through the filter and the collimator to form a moderated neutron beam, wherein the moderated neutron beam has an epithermal neutron flux of $1.7\times10^9$ n cm$^2$ s$^{-1}$ to $2.0\times10^9$ n cm$^{-2}$s$^{-1}$, and a fast neutron dose component of $2.0\times10^{-11}$ cGy cm$^2$ to $2.6\times10^{-11}$ cGy cm$^2$ per epithermal neutron.

13. The neutron beam source as claimed in claim 11, wherein:

the accelerator produces a proton beam of 30 MeV/2 mA for colliding the beryllium target to form neutrons; and the neutrons pass through the filter and the collimator to form a moderated neutron beam, wherein the moderated neutron beam has an epithermal neutron flux of $3.4\times10^9$ n cm$^{-2}$s$^{-1}$ to $4.0\times10^9$ n cm$^{-2}$s$^{-1}$, and a fast neutron dose component of $2.0\times10^{-11}$ cGy cm$^2$ to $2.6\times10^{-11}$ cGy cm$^2$ per epithermal neutron.

14. The neutron beam source as claimed in claim 4, further comprising a lead wall surrounding sidewalls of the filter.

15. The neutron beam source as claimed in claim 14, wherein the lead wall has a thickness of greater than or equal to 15 cm.

16. The neutron beam source as claimed in claim 4 being applied to accelerator-based boron neutron capture therapy.

* * * * *